United States Patent [19]

Stines

[11] Patent Number: 4,790,821
[45] Date of Patent: Dec. 13, 1988

[54] PRESSURE GAUGE AND SYSTEM

[75] Inventor: Joseph R. Stines, Poland, Ind.

[73] Assignee: Vance Products Incorporated, Spencer, Ind.

[21] Appl. No.: 88,682

[22] Filed: Aug. 24, 1987

[51] Int. Cl.[4] ............................................. A61M 25/00
[52] U.S. Cl. ....................................... 604/98; 604/100; 128/748; 73/706; 73/744
[58] Field of Search ............................... 128/672–686, 128/748; 73/744–746, 706–707, 741; 604/96–103

[56] References Cited

U.S. PATENT DOCUMENTS

| | | | |
|---|---|---|---|
| 2,437,440 | 3/1948 | Ridgen | 73/745 X |
| 2,498,366 | 2/1950 | Greer et al. | |
| 2,628,139 | 2/1953 | Gilliand | 73/744 X |
| 2,841,984 | 7/1958 | Green | |
| 2,986,938 | 6/1961 | Grandstaff | |
| 3,415,123 | 12/1968 | Broughton | |
| 3,442,134 | 5/1969 | Bennett et al. | 73/745 |
| 3,496,776 | 2/1970 | Mistarz | |
| 3,975,967 | 8/1976 | Conti | |
| 4,278,856 | 7/1981 | Owens | 73/744 X |
| 4,370,982 | 1/1983 | Reilly | |
| 4,508,103 | 4/1985 | Calisi | 128/748 X |
| 4,552,153 | 11/1985 | Newman et al. | 73/744 X |

Primary Examiner—Kyle L. Howell
Assistant Examiner—Angela D. Sykes
Attorney, Agent, or Firm—Woodard, Emhardt, Naughton Moriarty & McNett

[57] ABSTRACT

A pressure gauge which may be operably coupled to a fluid pressure supply device and a balloon catheter. The pressure gauge includes a mechanism which impedes a contaminant, such as corrosion and acid flux, from entering the pressurized fluid being measured. In one embodiment, this mechanism may include a piston positioned in a piston chamber. The piston has at least one, and preferably two, O-rings nested therearound to provide a seal with the piston chamber's wall. The piston may include an inter-gasket pressure chamber positioned between two O-rings which is communicated to the top or bottom of the piston, resulting in pressure equilibrium. Several inter-gasket pressure chambers may be provided.

19 Claims, 3 Drawing Sheets

PRESSURE GAUGE AND SYSTEM

BACKGROUND OF THE INVENTION

The present relates generally to pressure gauges and more specifically to pressure gauges having means integrated therein to confine corrosion contamination within the gauge from contaminating the fluid that is being measured.

While having other applications, the present invention is especially useful in the medical field in which balloon catheters are used. Balloon catheters, as known in the medical art, have various applications in which an inflatable balloon on the end of a catheter is inflated and/or deflated in the body of a patient. The inflation of such balloon is accomplished by a fluid, either a gas or liquid, and typically the pressure of such fluid is monitored. Although, in normal operation, the balloon and corresponding catheter provide a fluid-tight seal between the pressure-inflating fluid and the patient, there always remains the risk that the balloon and/or catheter supplying the balloon would develop a leak, causing the pressurized fluid to come in contact with the tissue of the patient. Should there be a contaminant in the pressurized fluid used to inflate the balloon catheter, such a leak would jeopardize the health of the patient.

Frequently, the balloon at the end of the catheter is located in a vessel in the patient's body and is not readily visible to the doctor utilizing the balloon catheter. Consequently, appropriate control over the balloon catheter is maintained by monitoring the pressure of the fluid supplied to the balloon. By previous experimentation, it is possible for the medical doctor to know how large the balloon will inflate as a function of the pressure in the fluid. Such fluid is typically monitored by a pressure gauge placed in series along the lines supplying pressurized fluid to the balloon. Unfortunately, a problem exists as to corrosive material from within the mechanical pressure gauge leaking into the pressurized fluid and migrating to the part of the balloon catheter located within the patient. Such contamination typically takes the form of corrosion and acid present from the use of acid flux in soldering and/or welding internal components of the pressure gauge. Typically, such pressure gauges are made of brass, resulting in a corresponding green corrosion mixed with the acid flux residue. This corrosion forms a "green goo" which, in some circumstances, can migrate into the balloon catheter, increasing the risk of contamination of the patient.

Efforts have been made to solve this problem, but have met with limited success. For example, some have tried compartmentalizing gold-plated nickel bellows in the pressure gauge to isolate the inner volume of the pressure gauge from the main line to which the gauge is attached. Unfortunately, this approach breaks down easily, is relatively expensive, and does not survive the necessary repeat sterilization of the pressure gauge. The bellows become degraded during sterilization, which is imperative in the medical field, resulting in an unsatisfactory design. Other approaches include attempts to use solvents and techniques to rinse the corrosion and acid flux residue from the pressure gauges. So far as is known to the inventor, this approach has had unsatisfactory results. Other rubber diaphrams have been unable to survive repeated sterilizations.

Various pressure gauges have been disclosed in United States patents. U.S. Pat. No. 2,986,938 to Grandstaff discloses a pressure gauge having a flexible diagram providing a seal between the fluid being measured and the pressure gauging device. Also, Grandstaff has a piston with O-rings and a longitudinal bore down the center of the piston. However, this longitudinal bore is plugged. U.S. Pat. No. 2,498,366 to Greer discloses an automatic gauge valve having a piston (reference no. 23) which acts as a valve body to regulate fluid flow. This piston includes a passage therethrough communicating the pressure gauge with the supply of pressurized fluid. The passage therethrough is obstructed by a check valve ball having a spring bias. U.S. Pat. No. 4,370,982 to Reilly discloses a device for inflating balloon catheters with a pressure gauge coupled thereto. U.S. Pat. No. 3,496,776 to Mistarz discloses a pressure gauge having a flexible diaphragm to seal contaminants in the pressure gauge from entering the measured fluid, such as milk. U.S. Pat. No. 2,841,984 to Green discloses a pressure gauge having a flexible membrane for transmitting fluid pressure. U.S. Pat. No. 3,415,123 to Broughton discloses a device having a piston mounted within a body member to be connected between an oil well drilling pipe and a pressure gauge to prevent drilling mud from entering the pressure gauge while allowing the drilling mud pressure to be transmitted to the gauge. U.S. Pat. No. 3,975,967 to Conti discloses a corrosion resistant bourdon tube used in a pressure gauge. While each of these devices provide certain advantages, none of them provide the same advantages in the same way as the present invention.

The present invention solves the problem of isolating the corrosion and other contamination from the main line to which the gauge must necessarily be attached and still assure reliable, accurate pressure gauge readings, following multiple sterilizations.

SUMMARY OF THE INVENTION

According to one embodiment, the present invention provides a pressure gauge comprising a body having a piston chamber disposed therein partially defined by a piston chamber wall; a piston disposed in the piston chamber and reciprocally movable therein, the piston having a first gasket and a second gasket coupled thereto and engaging the chamber wall, the first gasket and the second gasket partially defining a first inter-gasket pressure chamber therebetween, the piston having a piston channel therein, the piston channel communicating the piston chamber with the first inter-gasket pressure chamber; and means for measuring pressure in the piston chamber coupled to the body.

The present invention also provides, in combination, means for supplying fluid coupled to a balloon catheter, the means for supplying fluid providing a sterilized working fluid to the balloon catheter; and a pressure gauge operably coupled to the balloon catheter and including: (a) a body having a piston chamber disposed therein partially defined by a piston chamber wall; (b) a piston disposed in the piston chamber and reciprocally movable therein, the piston having a first gasket and a second gasket coupled thereto and engaging the chamber wall, the first gasket and the second gasket and the piston chamber wall and the piston define an inter-gasket pressure chamber therebetween; (c) means for measuring pressure in the piston chamber coupled to the body and isolated from the inter-gasket pressure chamber, the means for measuring containing a corrosion contaminated fluid above and in contact with the piston, wherein the working fluid from the means for supplying fluid contacting a top surface of the piston, the piston providing a seal between the working fluid and the corrosion contaminated fluid.

One object of the present invention is to provide an improved pressure gauge and system.

Related objects of the present invention are disclosed in the following description of the preferred embodiment.

DESCRIPTION OF THE PREFERRED EMBODIMENT

Figure 1:
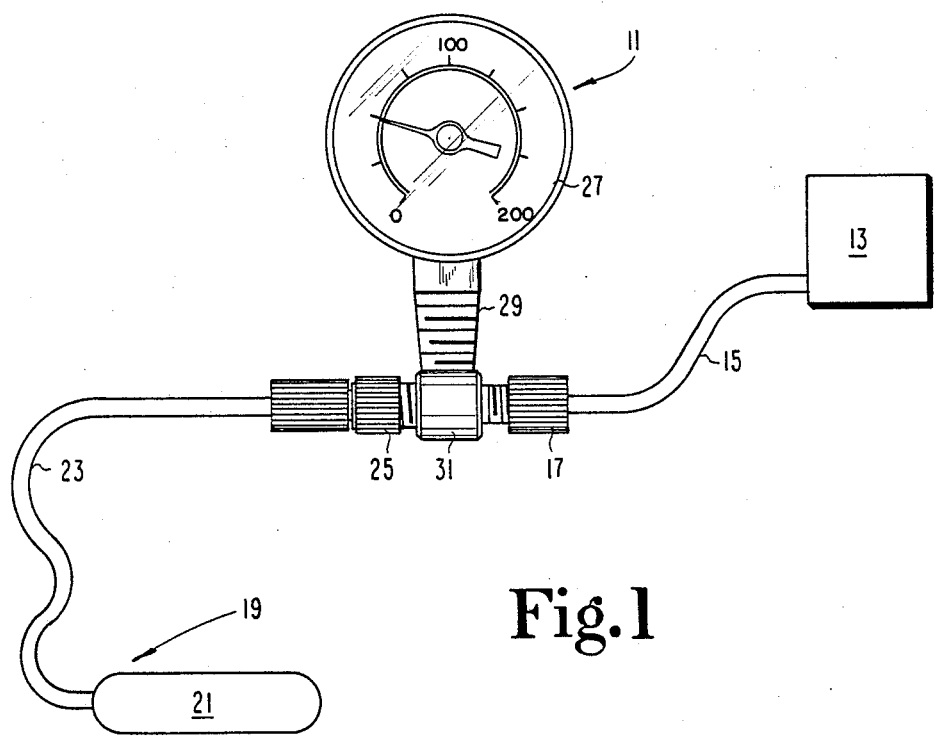
FIG. 1 shows a side view of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, pressure gauge 11 is coupled to fluid pressure supply device 13 by line 15 and coupler 17. Line 15 has a lumen therein to carry pressurized, sterilized working fluid supplied from fluid pressure supply device 13. Fluid pressure supply device 13 may be any of a number of mechanisms to supply pressurized fluid, a liquid, or a gas. It is believed that in the best mode, a pressurized fluid is sterilized water. Pressure gauge 11 is further coupled to balloon catheter 19 having balloon 21 located at the end of catheter 23. Catheter 23 has a lumen therein for delivery of the pressurized fluid to balloon 21. Catheter 23 is coupled to pressure gauge 11 by coupler 25. Thus, pressurized fluid from fluid pressure supply device 13 is supplied to balloon 21 by way of line 15 and catheter 23. Pressure gauge 11 is coupled in series therebetween to dynamically monitor the pressure in this main line supplying balloon 21. Pressure gauge 11 includes pressure dial 27 having a pressure needle thereon, threaded stem body 29 and main line housing 31 coupled thereto. Main line housing 31 includes male-threaded fittings which engage couplers 17 and 25. During the preferred use, balloon 21 is located in a medical patient.

Figure 2:
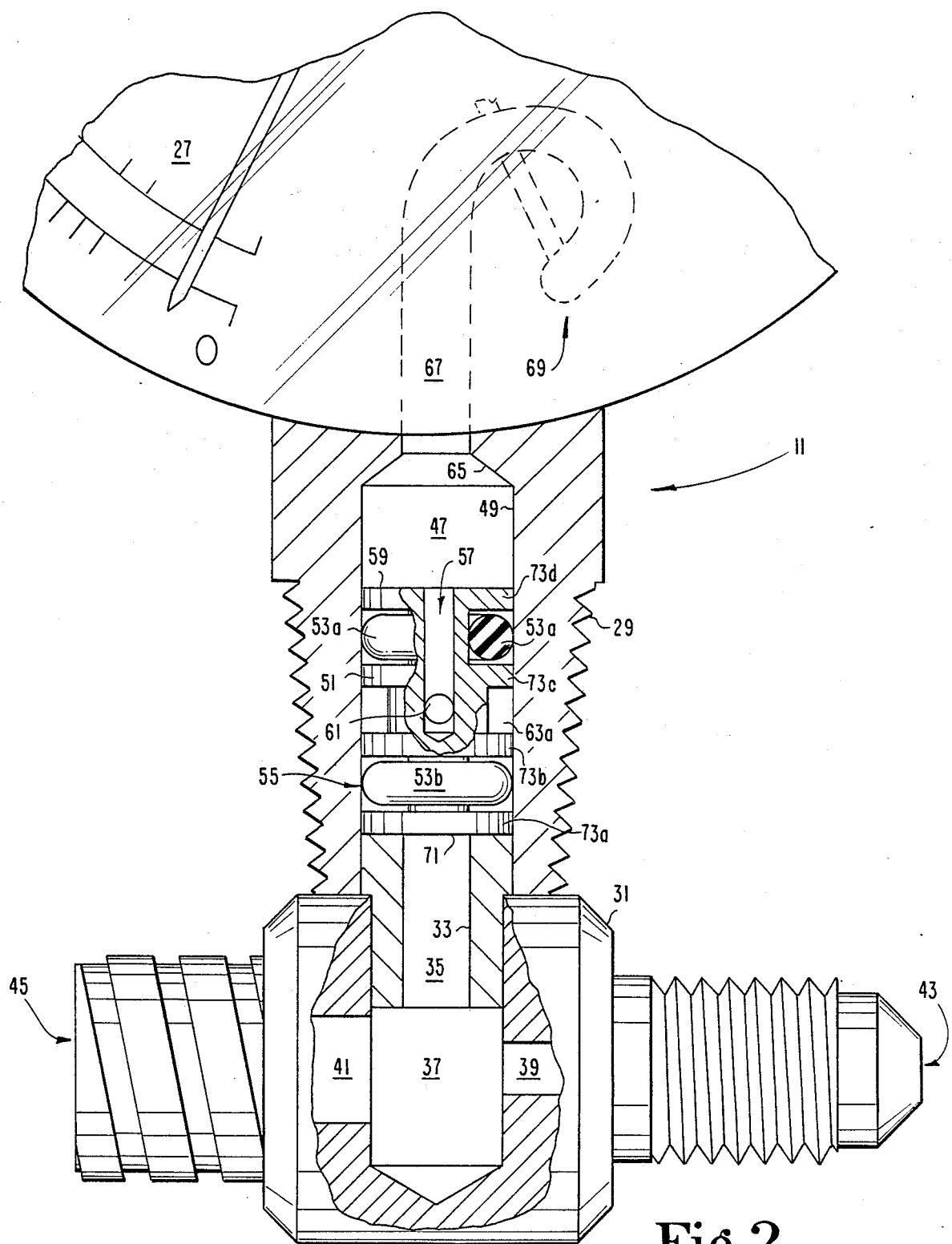
FIG. 2 shows a side elevation partial cut-away view of a pressure gauge of the present invention.

Referring now to FIG. 2, a detailed partial view of the pressure gauge shown in FIG. 1 is shown. Couplers 17 and 25 have been detached from the male-threaded stems and pressure dial 27 is only partially shown. Threaded stem body 29 is shown in section and main line housing 31 is shown in partial cut-away. Stem 29 is coupled to main line housing by tubular fitting 33 (shown in section) which has longitudinal bore 35 therein. Tubular fitting 33 has a cylindrical outer shape and is snuggly friction-fit down into main line housing 31. Furthermore, glue or other suitable sealing (not shown) may be used to further strengthen and seal the fit between the fitting 33 and housing 31. Longitudinal bore 35 communicates with main line housing chamber 37 which is centrally located therein. Main line housing chamber 37 is fabricated in housing 31 by machining a vertical bore downwardly into the solid main line housing. Housing chamber 37 further communicates with lateral bores 39 and 41 which communicate with fluid pressure openings 43 and 45, respectively. Openings 43 and 45 communicate with line 15 and catheter 23 as shown in FIG. 1.

Stem 29 has a longitudinal bore therethrough defining piston chamber 47. Piston chamber 47 has cylindrical wall 49 which, in the preferred embodiment, is round when viewed from a top section with a constant cross-sectional diameter up and down piston chamber 47. Pressure piston 51 (shown in partial cut-away) is located in piston chamber 47. Piston 51 includes gaskets or O-rings 53a and 53b. These O-rings, in the best mode, are round in cross-section and are made of neoprene rubber. Other suitable elastomeric material may be used for the O-rings. O-rings 53a and 53b contact cylindrical wall 49 along their outermost circumference, each forming a seal, such as seal 55. Pressure piston 51 has an unobstructed longitudinal piston bore 57 which penetrates piston top surface 59 and communicates with unobstructed radial piston bore 61. Longitudinal piston bore 47 and radial piston bore 61 collectively form a piston channel. This piston channel provides pressure communication and consequently, pressure equilibrium, between that portion of piston chamber 47 above piston top surface 59 and inter-gasket pressure chamber 63a. Note that bottom surface 71 of the piston is unpenetrated by the piston channel, thus maintaining the seal.

The piston, as shown, may be utilized having no piston channel therein. Such a solid piston is the same as shown in FIGS. 2–5, but with no longitudinal or radial bores therein. However, the best mode includes the piston channel, which in addition to providing pressure equilibrium, as discussed above, also provides lubrication of the O-rings on the sides facing the inter-gasket pressure chamber. Inter-gasket pressure chamber 63a is defined as the volume in piston chamber 47 between the respective seal of O-rings 53a and 53b and the piston and piston chamber wall.

Chamber 47 is coupled to the analog pressure readout mechanism behind dial 27 by way of frusto-conical portion 65, tube 67 (shown in phantom lines), and actuating coil 69 as is well known in the pressure gauge art. Chamber 47, frusto-conical portion 65, and tube 67 are filled with a fluid, sterilized water in the best mode, to effect a pressure reading. Stem body 29, in the best mode, is made of brass. Likewise, main line housing 31 and tubular fitting 33 are, in the best mode, made of brass. Brass exhibits a relatively low corrosivity when exposed to water, and thus is well suited for the present invention. Nevertheless, corrosion contaminated water is present in tube 67 and contacts top surface 59 of the piston. Pressure piston 51, in the best mode, in constructed of a unitary piece of aluminum. Aluminum is believed to be suitable due to its relatively low corrosivity in water and relatively light weight.

In operation, the device of FIG. 2 measures fluid pressure while affording protection against contamination of the fluid being measured by contaminants located in the upper portion of piston chamber 47, the frusto-conical portion 65, tube 67, and coil 69. Typically, these contaminants constitute corrosion and residue from acid flux occurring in the valve mechanism due to soldering and/or welding of metal components in the valve mechanism. Typically, acid flux is used to prepare metal surfaces for soldering, but due to its acidic nature, causes some subsequent corrosion. With metal, such as brass, this corrosion is generally green in color, forming a "green goo" having undesirable properties. Since piston 51 is movable in chamber 47, it mechanically transmits fluid pressure from the sterilized working fluid from longitudinal bore 35, across piston bottom surface 71 into the fluid in chamber 47 above top surface 59. The working fluid contacts surface 71 since there is no diaphragm susceptible to destruction during sterilization. Yet, piston 51 provides a seal between the working fluid and the contaminated fluid contacting top surface 59. Due to the relatively small and lightweight nature of rigid, reciprocally movable piston 51, an accurate pressure transmission occurs without undue effect due to the weight of piston 51. Furthermore, undue friction is avoided between O-rings 53a and 53b and cylindrical wall 49. This undue friction is due to the careful sizing of the O-rings to closely corresponding with the shape of cylindrical wall 49, and to the pressure equilibrium afforded by longitudinal piston bore 57 and radial piston bore 61. This pressure equilibrium occurs in inter-gasket pressure chamber 63a. Consequently, there is not a significant pressure differential across the O-rings which would cause deflection of the O-rings, typically towards each other. Consequently, the O-rings may be sized such that they radially bear against cylindrical wall 49 with a relatively small force normal thereto. With a relatively small normal force, the consequent frictional force resisting reciprocal movement of piston 51 is small. In the same spirit, it is believed to be preferred to use O-rings which have a relatively smooth outer surface and a relatively low coefficient of friction for the elastomeric material, and desirable to have cylindrical wall 49 finished with a smooth surface. Teflon may be used to this end. A net result is a great seal between the O-rings and the cylindrical wall while avoiding undue friction in reciprocal movement of piston 51.

As seen in FIG. 2, due to the existence of bore 57 and bore 61, the upper portion of piston chamber 47 (that portion above piston top surface 59) is not completely sealed or isolated from inter-gasket pressure chamber 63a. However, bores 57 and 61 do provide a tortured path through which movement of any "green goo" or other foreign substance is impeded. The most complete seal between chamber 47 and chamber 37 is provided by O-ring 53b at seal 55. Nevertheless, it is believed that the pressure equilibrium provided by bores 57 and 61 provides a greater overall benefit to the present invention than if they were not present. However, when piston 51 does not include the piston channel, then inter-gasket pressure chamber 63a is sealed by O-ring 53a, or isolated, from the fluid and tube 67 above top surface 59 of the piston.

Note that in the preferred embodiment, piston 51 has four radial discs 73a, 73b, 73c and 73d. These radial discs correspond to the cylindrical profile of cylinder 49, yet have a slighty smaller diameter so as to eliminate or greatly reduce contact therewith. Consequently, the radial discs do not provide a complete pressure seal to fluids. However, the discs do hold the O-rings and further provide a tortured path to resist migration of contaminants from tube 67 down into chamber 37.

Figure 4:
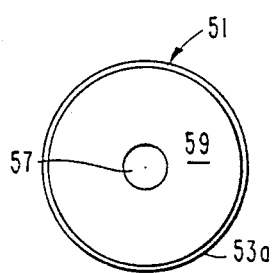
FIG. 4 shows a top plan view of the pressure piston utilized in the gauge of FIG. 2.
Figure 3:
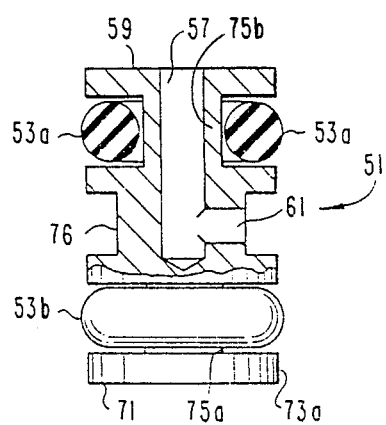
FIG. 3 shows a side elevation partial cut-away view of a pressure piston utilized in the gauge of FIG. 2.

Referring now to FIGS. 3 and 4, pressure piston 51 is shown in isolation, removed from pressure gauge 11. FIG. 3 shows a partial cutaway view, and is shown in an orientation rotated 90° from that shown in FIG. 2, allowing a side view of radial piston bore 61. Radial discs, such as radial disc 73a on the bottom of piston 51, are shown. Between these radial discs are interstatial members rigidly connecting the discs together. These include O-ring interstatial members 75a and 75b and inter-gasket pressure chamber interstatial member 76. The radial discs and interstatial members form a pressure piston which has a series of annular grooves therein, creating a tortured path for contaminants to migrate across while providing a piston which will maintain proper alignment within piston chamber 47. Piston 51, in the preferred embodiment, is small, about 8½ mm tall and 5 mm in diameter.

Figure 5:
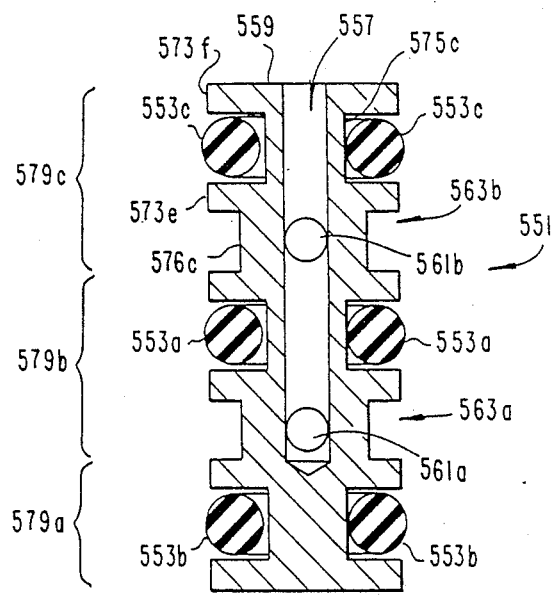
FIG. 5 shows a side elevation view in full section of an alternative embodiment of a pressure piston utilized in the present invention.

Referring now to FIG. 5, an alternative embodiment of pressure piston 51 as shown in FIGS. 2–4 is illustrated. In FIG. 5, reference numerals begin "500" series to denote their alternative embodiment structure, but the corresponding tens and unit digits are substantially similar to those discussed with the previous figures. For example, pressure piston 551 corresponds to pressure piston 51. In FIG. 5, pressure piston 551 is substantially the same as pressure piston 51 of FIG. 3 except that pressure piston 51 has three stages 579a, 579b, and 579c, instead of two stages as shown in the piston of FIG. 3. Correspondingly, there are three O-rings 553a, 553b and 553c positioned around interstatial members of the piston. Note that piston 551 is essentially identical to piston 51 except that stage 579c has been added to the top thereof. Correspondingly, top surface 559 is formed. The new three-stage arrangement as shown has a longer longitudinal piston bore 557 which communicates with radial piston bore 561a and radial piston bore 561b. Correspondingly, when piston 551 is placed in a piston chamber (such as piston chamber 47 of FIG. 2), two inter-gasket pressure chambers are formed. These inter-gasket pressure chambers are formed at 563a between O-rings 553a and 553b, and at 563b between O-rings 553c and 553a. Stage 579c includes the additional inter-gasket pressure chamber interstatial member 576c, O-ring interstatial member 575c, and radial discs 573e and 573f.

Just as piston 551 shows the addition of stage 579c to the embodiment shown in FIG. 3 of piston 51, further stages may be added. In this way, embodiments practiced in the present invention may be utilize not only two-stage or three-stage pistons, as shown in FIGS. 3 and 5, respectively, but four-, five-, six-, seven-, eight-, nine- or ten-stage pistons, or even pistons utilizing more than ten stages. Generally, the larger the number of stages used per piston results in a greater seal against contamination. A correspondingly larger degree of friction is developed. It is believed that the best mode of the present invention utilizes a two-stage piston as shown in FIGS. 2 and 3. As pistons having a greater number of stages are used, stems and piston chambers, such as stem 29 and piston chamber 47, are correspondingly elongated to accommodate the longer multi-staged pistons.

The present device may also be used with a single-stage, such as 579a, instead of multiple-stage pistons shown in FIGS. 3 and 5. Furthermore, the present device may have a longitudinal piston bore, such as longitudinal piston bore 57, downwardly oriented such that it penetrates piston bottom surface 71 (see FIG. 2) instead of piston top surface 59.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A pressure gauge comprising:
    a body having a piston chamber disposed therein partially defined by a piston chamber wall;
    a piston disposed in said piston chamber and reciprocally movable therein, said piston having a first gasket and a second gasket coupled thereto and engaging said chamber wall, said first gasket and said second gasket partially defining a first inter-gasket pressure chamber therebetween, said piston having a piston channel therein, said piston channel communicating said piston chamber with said first inter-gasket pressure chamber; and
    means for measuring pressure in said piston chamber coupled to said body.

2. The gauge of claim 1 wherein said piston further includes a first radial disc, a second radial disc, a third radial disc, and a fourth radial disc, wherein said first gasket is a first O-ring disposed between said first radial disk and said second radial disc, and wherein said second gasket is a second O-ring disposed between said third radial disc and said fourth radial disc.

3. The gauge of claim 2 wherein said piston channel includes an unobstructed longitudinal piston bore and an unobstructed radial piston bore.

4. The gauge of claim 3 wherein said piston has a first surface and a second surface, said piston channel penetrating said first surface, said second surface being unpenetrated by said piston channel.

5. The gauge of claim 4 wherein said piston chamber wall is completely cylindrical between said first gasket and said second gasket.

6. The gauge of claim 5 wherein said piston further includes a third gasket coupled thereto and engaging said piston chamber wall, said third gasket and said second gasket partially defining a second inter-gasket pressure chamber therebetween.

7. The gauge of claim 6 wherein said second inter-gasket pressure chamber communicates with said piston chamber.

8. The gauge of claim 7 wherein said piston comprises aluminum.

9. The gauge of claim 8 wherein said first O-ring is made of neoprene rubber, and wherein said second O-ring is made of neoprene rubber.

10. The gauge of claim 9 and further comprising:
    a main line housing coupled to said body and adapted to be coupled to a fluid pressure supply source; and
    a balloon catheter coupled to said main line housing.

11. The gauge of claim 1 wherein said piston channel includes an obstructed longitudinal piston bore and an unobstructed radial piston bore.

12. The gauge of claim 1 wherein said piston has a first surface and a second surface, said piston channel penetrating said first surface, said second surface being unpenetrated by said piston channel.

13. The gauge of claim 1 wherein said piston chamber wall is completely cylindrical between said first gasket and said second gasket.

14. The gauge of claim 1 wherein said piston further includes a third gasket coupled thereto and engaging said piston chamber wall, said third gasket and said second gasket partially defining a second inter-gasket pressure chamber therebetween.

15. The gauge of claim 1 wherein said second inter-gasket pressure chamber communicates with said piston chamber.

16. The gauge of claim 1 wherein said piston comprises aluminum.

17. The gauge of claim 1 wherein said first gasket is made of neoprene rubber, and wherein said second gasket is made of neoprene rubber.

18. The gauge of claim 1 and further comprising:
    a main line housing coupled to said body and adapted to be coupled to a fluid pressure supply source; and
    a balloon catheter coupled to said main line housing.

19. In combination:
    a sterilized balloon catheter;
    means for supplying sterilized fluid coupled to said balloon catheter, said means for supplying fluid providing a sterilized working fluid to said balloon catheter; and
    a sterilized pressure gauge operably coupled to said balloon catheter and including:
    (a) a body having a sterilized piston chamber disposed therein partially defined by a piston chamber wall;
    (b) a piston disposed in said piston chamber and reciprocally movable therein, said piston having a first gasket and a second gasket coupled thereto and engaging said chamber wall, said first gasket and said second gasket and said piston chamber wall and said piston define an inter-gasket pressure chamber therebetween; and
    (c) means for measuring pressure in said piston chamber coupled to said body and isolated from said inter-gasket pressure chamber, said means for measuring containing a corrosion contaminated fluid above and in direct contact with said piston, wherein said working fluid from said means for supplying fluid contacting said piston, said piston providing a seal between said working fluid and said corrosion contaminated fluid.

* * * * *

UNITED STATES PATENT AND TRADEMARK OFFICE
CERTIFICATE OF CORRECTION

PATENT NO. : 4,790,821

DATED : December 13, 1988

INVENTOR(S) : Joseph R. Stines

It is certified that error appears in the above-identified patent and that said Letters Patent is hereby corrected as shown below:

In Column 4, line 28, change "47" to --57--.

In Column 7, line 31, change "disk" to --disc--.

Signed and Sealed this

Sixteenth Day of May, 1989

Attest:

DONALD J. QUIGG

*Attesting Officer*      Commissioner of Patents and Trademarks